United States Patent
Yuang

(10) Patent No.: US 6,553,266 B1
(45) Date of Patent: Apr. 22, 2003

(54) UNDERPANTS STRUCTURE PROVIDED WITH MEANS TO AUGMENT PERINEAL MUSCLES

(76) Inventor: Jui-Kuang Yuang, 6/F, Number 22-5, YuanYuan Road, Sanmin Chiu, Kaohsiung (TW)

(*) Notice: Subject to any disclaimer, the term of this patent is extended or adjusted under 35 U.S.C. 154(b) by 0 days.

(21) Appl. No.: 10/175,476

(22) Filed: Jun. 18, 2002

(51) Int. Cl.[7] ................................. A61N 1/05
(52) U.S. Cl. .................. 607/138; 607/143; 607/39; 607/41
(58) Field of Search ................. 607/39, 40, 41, 607/143, 142, 138; 600/386, 388, 29, 30

(56) References Cited

U.S. PATENT DOCUMENTS 4,205,671 A * 6/1980 Lassen ................... 128/886
5,871,533 A * 2/1999 Boutos ................... 607/138
5,871,534 A * 2/1999 Messick et al. ............ 607/138

* cited by examiner

Primary Examiner—Jeffrey R. Jastrzab
(74) Attorney, Agent, or Firm—Raymond Y. Chan; David and Raymond Patent Group

(57) ABSTRACT

An underpants structure comprises a left waistband, a right waistband, a seat, and a pulsating current generator. The left waistband, the right waistband, and the seat are joined together to form a waist hole, a left leg hole, and a right leg hole. The seat is provided with an opening and an electrically-conductive rubber sheet attached to the inner side of the seat such that the rubber sheet is corresponding in location to the perineum of a male person. The seat covers the buttocks of the male person such that the penis and the scrotum of the male person are extended out of the seat via the opening of the seat, and that the rubber sheet comes in contact with the perineum of the male person. The rubber sheet is provided with a low frequency pulsating current by the pulsating current generator.

2 Claims, 4 Drawing Sheets

UNDERPANTS STRUCTURE PROVIDED WITH MEANS TO AUGMENT PERINEAL MUSCLES

FIELD OF THE PRESENT INVENTION

The present invention relates generally to underpants, and more particularly to an underpants structure which is provided with means to furnish a low frequency pulsating current to stimulate the muscles of perineum of a person wearing the underpants structure.

BACKGROUND OF THE INVENTION

The impotence, the vaginal laxity, and the female stress urinary incontinence are attributable to the aging of the perineal muscles. The contraction and the expansion of bulbocavernosus and ischiocavernosus play an important role in the human sexual intercourse such that they enable the spongy tissue in the penis to fill-with blood so as to bring about the erection of the penis, and that the clitoris is filled with blood to become swollen and rigid, thereby resulting in orgasm in the female. In addition, an augmentation of contraction and expansion of ischiocavernosus is helpful in discharge of residual urine from the urethra in the male, and in prevention of urinary incontinence in the female. Such genital disorders as described above can not be cured completely by drugs or surgical treatment.

A conventional physical therapy involves the application of an electrically-conductive rubber piece to the perineal cavity so as to stimulate the muscles in perineum with a low frequency pulse. The conventional physical therapy is defective in design in that the conductive rubber piece is often not attached properly to the perineum of a subject, thereby undermining the effectiveness of the physical therapy. In addition, the subject must remain in the stationary state while the therapy is in progress, so as to prevent the displacement of the conductive rubber piece. Furthermore, the conductive rubber piece is of a sheetlike construction and can not be therefore inserted into vagina to effect the treatment of perineal muscles of the vagina.

SUMMARY OF THE INVENTION

The primary objective of the present invention is to provide an underpants structure comprising a pant which is provided with an electrically-conductive rubber piece corresponding in location to perineum in the male. The electrically-conductive rubber piece is insusceptible to displacement regardless of the posture of a wearer thereof It is another objective of the present invention to provide an underpants structure comprising a panty which is provided with a soft projection of silicone rubber corresponding in location to the vaginal opening. The projection is covered with an electrically-conductive rubber layer. The panty is worn by a female person such that the projection is inserted into the vagina, and that the electrically-conductive rubber layer is then connected electrically to a pulsating current supplying unit so as to stimulate the vagina, thereby resulting in augmentation of perineal muscles.

The primary objective of the present invention is to provide an underpants structure comprising a pant which is provided with an electrically-conductive rubber piece corresponding in location to perineum in the male. The electrically-conductive rubber piece is insusceptible to displacement regardless of the posture of a wearer thereof It is another objective of the present invention to provide an underpants structure comprising a panty which is provided with a soft projection of silicone rubber corresponding in location to the vaginal opening. The projection is covered with an electrically-conductive rubber layer. The panty is worn by a female person such that the projection is inserted into the vagina, and that the electrically-conductive rubber layer is then connected electrically to a pulsating current supplying unit so as to stimulate the vagina, thereby resulting in augmentation of perineal muscles.

The features and the advantages of the present invention will be more readily understood upon a thoughtful deliberation of the following detailed description of the preferred embodiments of the present invention with reference to the accompanying drawings.

DETAILED DESCRIPTION BRIEF DESCRIPTION OF DRAWINGS

DETAILED DESCRIPTION OF THE PREFERRED EMBODIMENT

Figure 1:
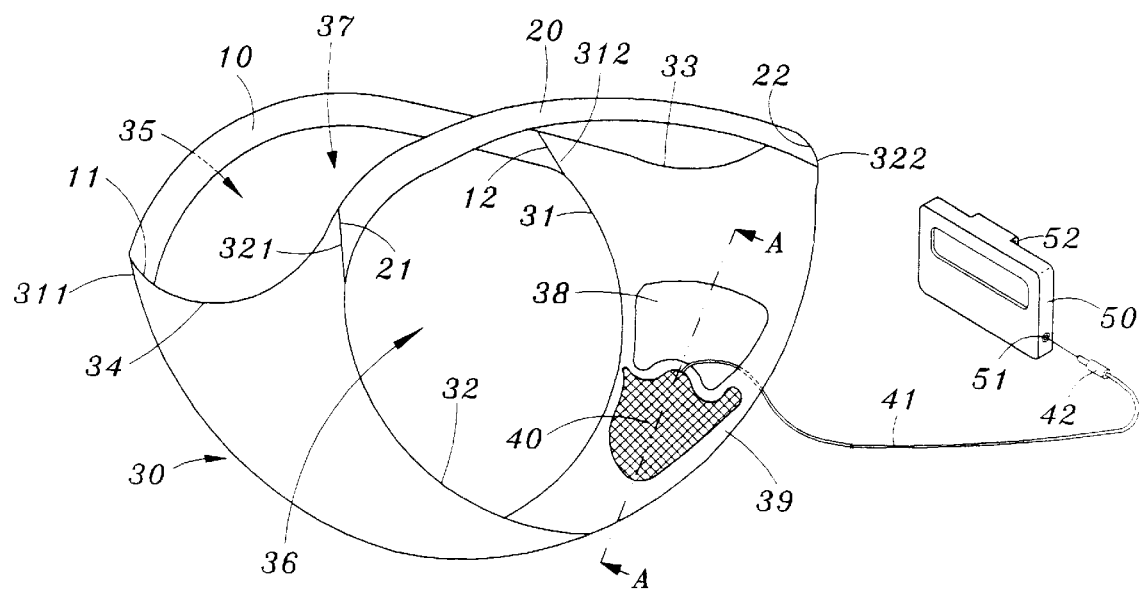
FIG. 1 shows a perspective view of a first preferred embodiment of the present invention.
Figure 2:
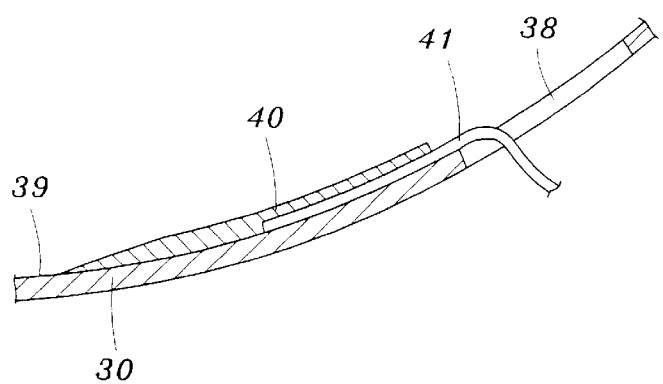
FIG. 2 shows a sectional view of a portion taken along the direction indicated by a line A—A as shown in FIG. 1.
Figure 3:
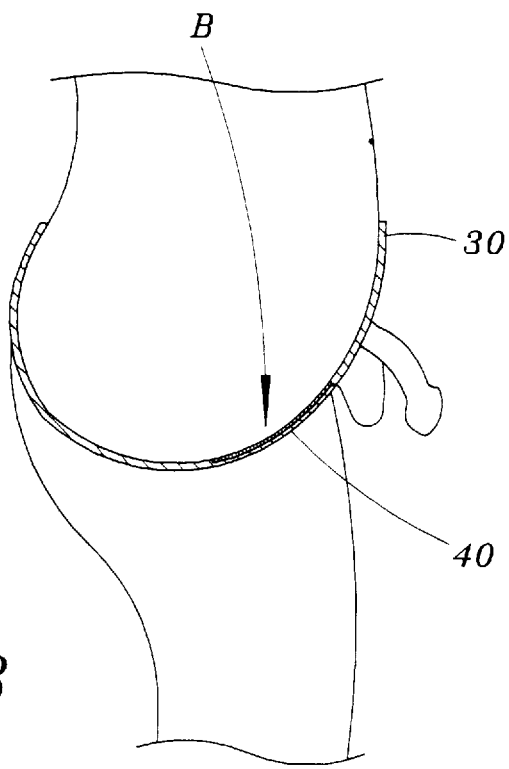
FIG. 3 shows a side sectional schematic view of the first preferred embodiment of the present invention worn by a male person.

As show in FIGS. 1–3, an underpants structure of the first preferred embodiment of the present invention is intended to be used by a male person and is formed of a left waistband 10, a right waistband 20, and a seat 30 covering the buttocks.

The left waistband 10 is expandable and provided with a first end 11 and a second end 12 opposite to the first end 11.

The second waistband 20 is expandable and provided with a first end 21 and a second end 22 opposite to the first end 21.

The seat 30 has a left fringe 31, a right fringe 32, a front fringe 33, and a rear fringe 34. The left fringe 31 has one end 311,which is connected with the first end 11 of the left waistband 10. The left fringe 31, further has other end 312, which is connected with the second end 12 of the left waistband 10. As a result, a left leg hole 35 is formed by the left fringe 31 and the left waistband 10. The right fringe 32 has one end 321, which is connected with the first end 21 of the right waistband 20. The right fringe 32 further has other end 322,which is connected with the second end 22 of the right waistband 20. As a result, a right leg hole 36 is formed and defined by the right fringe 32 and the right waistband 20. A waist hole 37 is formed and defined by the front fringe 33, the rear fringe 34, the left waistband 10, and the right waistband 20. The seat 30 is provided with an opening 38 which is separated from the front fringe 33 by an appropriate distance. The seat 30 is used to cover the buttocks of a male person such that penis and scrotum of the male person are exposed via the opening 38 of the seat 30, as shown in FIG.

3. The seat 30 is further provided in an inner side 39 thereof with an electrically-conductive rubber sheet 40 attached thereto such that the rubber sheet 40 is located under the opening 38, as shown in FIGS. 1 and 2. The rubber sheet 40 is corresponding in location and size to perineum of the male person. The rubber sheet 40 is provided with a bonding wire 41 which is provided at an outer end thereof with a plug 42, as shown in FIG. 1.

The underpants structure of the present invention is used by a male person such that the seat 30 covers the buttocks of the male person, and that the left leg and the right leg of the male person are put respectively through the left leg hole 35 and the right leg hole 36, and further that penis and scrotum of the male person are exposed via the opening 38, and still further that the electrically-conductive rubber sheet 40 comes in close contact with perineum "B" of the male person, as illustrated in FIG. 3. The underpants structure of the present invention provides wearing comfort to a wearer. In addition, the rubber sheet 40 remains in close contact with perineum "B" of the wearer regardless of the posture of the wearer.

Figure 4:
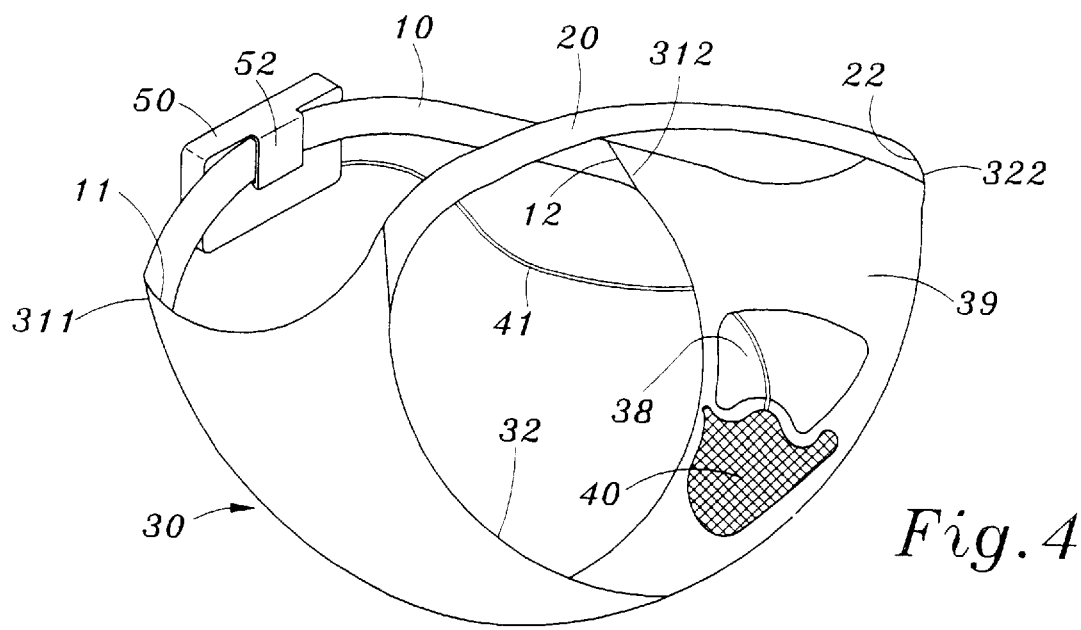
FIG. 4 shows a schematic view of a pulsating current supplying unit attached to a left waistband of the first preferred embodiment of the present invention.

As shown in FIGS. 1,3, and 4, the underpants structure of the present invention works to augment muscles of the perineum "B" of a male person in such a way that the plug 42 of the bonding wire 41 is inserted into a current output hole 51 of a pulsating current supplying unit 50, and that a low frequency pulsating current is transmitted to the rubber sheet 40 by the bonding wire 41 so as to stimulate the perineum "B" of the male person. The pulsating current supplying unit 50 comprises a hook 52 by which the unit 50 can be retained by the left waistband 10, as shown in FIG. 4.

Figure 5:
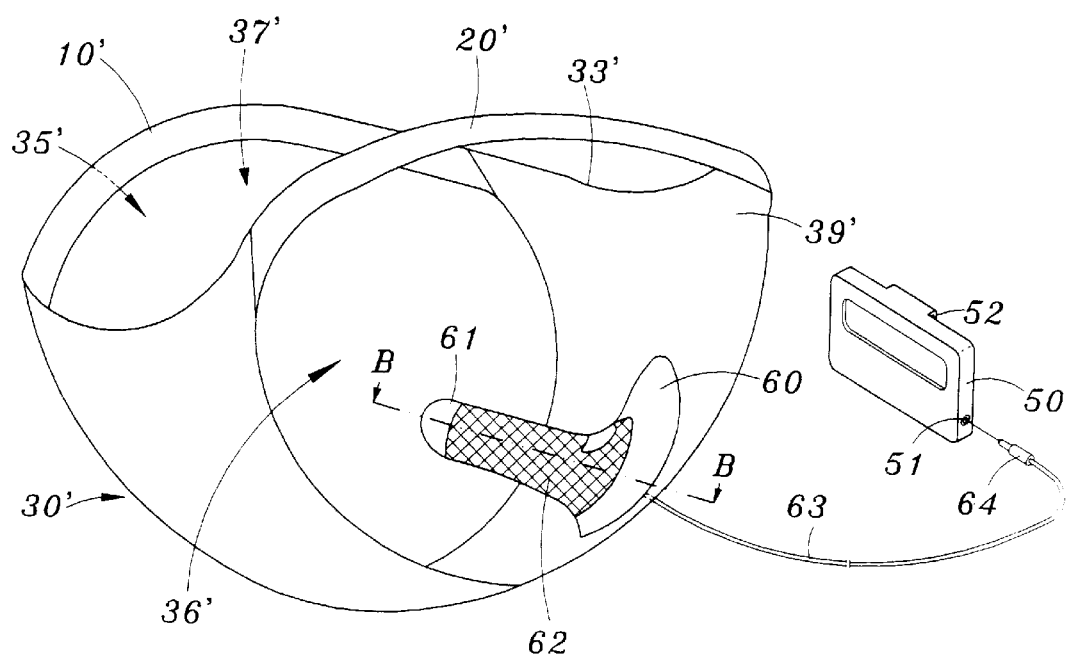
FIG. 5 shows a perspective view of a second preferred embodiment of the present invention.
Figure 6:
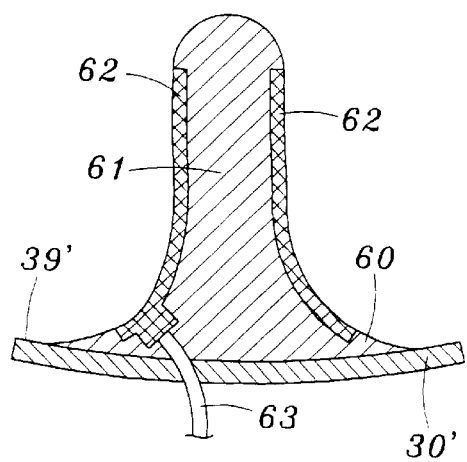
FIG. 6 shows a sectional view of a portion taken along the direction indicated by a line B—B as shown in FIG. 5.
Figure 7:
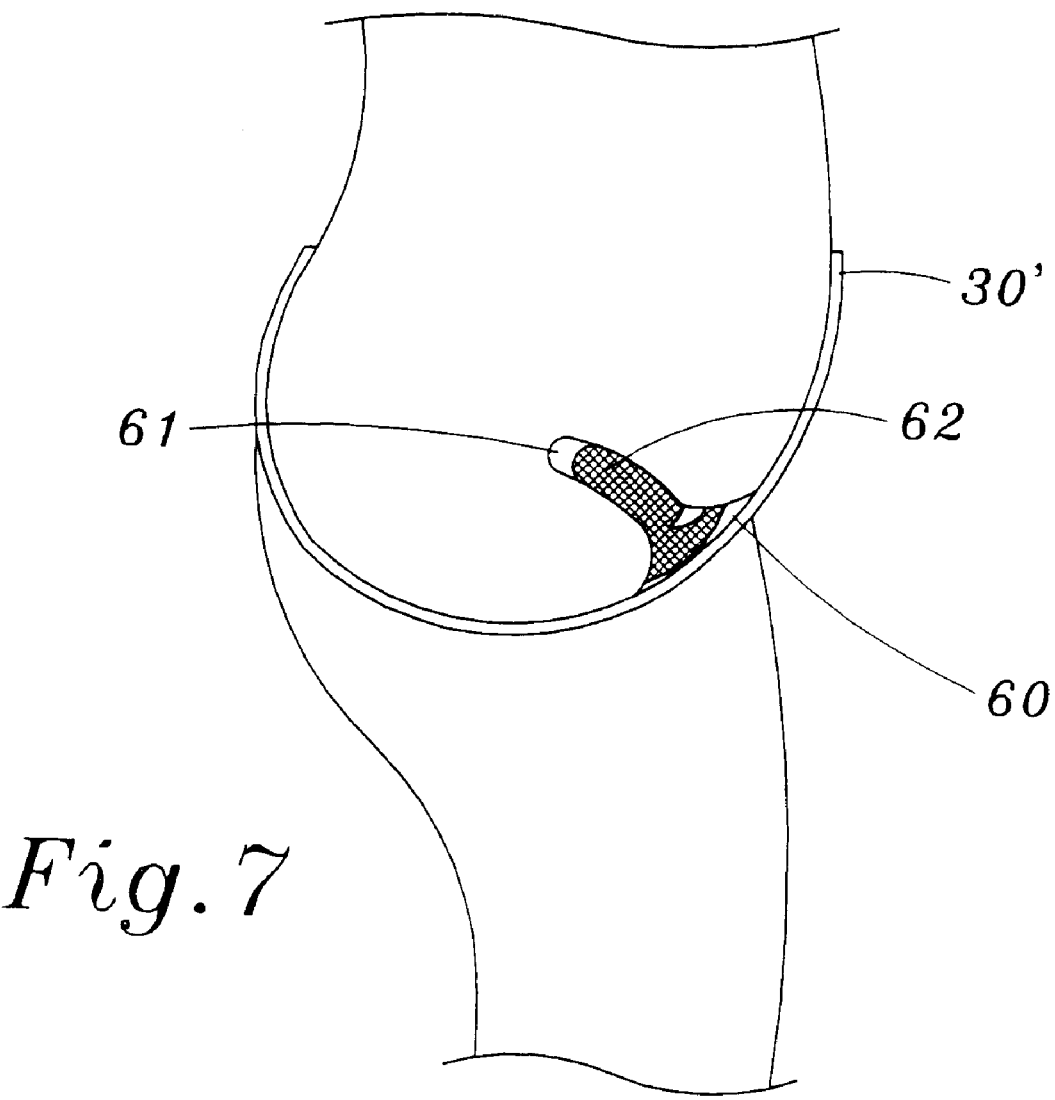
FIG. 7 shows a side sectional schematic view of the second preferred embodiment of the present invention worn by a female person.

As shown in FIGS. 5–7, an underpants structure of the second preferred embodiment of the present invention is designed to be used by a female person and is basically similar in construction to the underpants structure of the first preferred embodiment of the present invention, except that the female underpants structure of the pcesent invention is provided in an inner side 39' of a seat 30' with a soft base 60, which is separated from a front fringe 33' of the seat 30' by an appropriate distance. The soft base 60 is made of a silicone rubber material and is extended in the direction towards the interior of the female underpants structure. The soft base 60 is corresponding in location to vaginal opening and is provided with a soft projection 61 of the silicone rubber material. The soft projection 61 is extended in the direction toward the interior of the female underpants structure such that the soft projection 61 is comfortably inserted into the vagina of a female wearer of the present invention. The projection 61 is covered with an electrically-conductive rubber sheet 62, which is provided with a bonding wire 63 connected thereto. The bonding wire 63 is provided at the outer end with a plug 64, which is inserted into the current output hole 51 of the pulsating current supplying unit 50 so as to furnish the low frequency pulsating current to the rubber sheet 62 in an intimate contact with the vaginal wall.

The embodiments of the present invention described above are to be regarded in all respects as being illustrative and nonrestrictive. Accordingly, the present invention may be embodied in other specific forms without deviating from the spirit thereof The present invention is therefore to be limited only by the scopes of the following claims.

What is claimed is:

1. A male underpants structure comprising:

a left waistband of a length and having a first end and a second end opposite to said first end;

a right waistband of a length and having a first end and a second end opposite to said first; and a seat having a left fringe, a right fringe opposite to said left fringe, a front fringe, and a rear fringe opposite to said front fringe, said seat being joined with said left waistband in such a manner that one end of said left fringe of said seat is connected with said first end of said left waistband, and that other end of said left fringe of said seat is connected with said second end of said left waistband, thereby resulting in formation of a left leg hole between said left fringe of said seat and said left waistband, said seat further being joined with said right waistband in such a manner that one end of said right fringe of said seat is connected with said first end of said right waistband, and the other and of said right fringe of said seat is connected with said second end of said right waistband, thereby resulting in formation of a right leg hole between said right fringe of said seat and said right waistband, said front fringe and said rear fringe of seat forming a waist hole along with said left waistband and said right waistband, said seat being provided with an opening and an electrically-conductive rubber sheet attached thereto such that said rubber sheet is corresponding in location to the perineum of a male person, said opening of said seat being corresponding in location to the penis and scrotum of the male person whereby said seat covers the buttocks of the male person, with the penis and the scrotum of the male person being exposed via said opening of said seat, and with said rubber sheet being in close contact with the perineum of the male person, said rubber sheet being provided with a bonding wire fastened therewith, and a plug fastened at an outer end of said bonding wire.

2. A female underpants structure comprising:

a left waistband of a length and having a first end and a second end opposite to said first end;

a right waistband of a length and having a first end and a second end opposite to said first end; and a seat having a left fringe, a right fringe opposite to said left fringe, a front fringe, and a rear fringe opposite to said front fringe, said seat being joined with said left waistband in such a manner that one end of said left fringe of seat is connected with said end of said left waistband, and that other end of said left fringe of said seat is connected with said second end of said left waistband, thereby resulting in formation of a left leg hole between said left fringe of said seat and said left waistband, said seat further being joined with said right waistband in such a manner that one end of said right fringe of said seat is connected with said first end of said right waistband, and the other end of said right fringe of said seat is connected with said second end of said right waistband, thereby resulting in formation of a right leg hole between said right fringe of said seat and said right waistband, said front fringe and said rear fringe of said seat forming a waist hole along with said left waistband and said right waistband, said seat being provided in an inner side with a base attached thereto such that said base is corresponding in location to the vaginal opening of a female person, said base being made of a material having a softness, said base being provided with a projection extending therefrom such that said projection extends toward an interior of said seat, said projection being covered with an electrically-connected rubber sheet, said rubber sheet being provided with a bonding wire fastened therewith, and a plug fastened at an outer end of said bonding wire whereby said seat covers the buttocks of the female person such that said projection is inserted into vagina of the female person; and a pulsating current supplying unit for generating a low frequency pulsating current, said unit comprising a current output hole engageable with said plug of said bonding wire of said rubber sheet of said projection.

\* \* \* \* \*